United States Patent [19]

Craig et al.

[11] Patent Number: 5,686,657
[45] Date of Patent: Nov. 11, 1997

[54] PLANAR MANIFOLD ASSEMBLY

[75] Inventors: Stephen R. Craig; Paul B. Welsh, both of Wilmington, Del.; Robert C. Henderson, Avondale, Pa.

[73] Assignee: Hewlett-Packard Company, Palo Alto, Calif.

[21] Appl. No.: 678,844

[22] Filed: Jul. 12, 1996

Related U.S. Application Data

[63] Continuation of Ser. No. 376,614, Jan. 23, 1995, Pat. No. 5,567,868.

[51] Int. Cl.⁶ ............................................. G01N 30/04
[52] U.S. Cl. ............................................. 73/23.42
[58] Field of Search ............................. 137/269, 884; 73/23.35, 23.41, 23.42, 863.71, 863.72, 863.73

[56]     References Cited

U.S. PATENT DOCUMENTS

| | | | |
|---|---|---|---|
| 3,213,883 | 10/1965 | Carls | 137/884 |
| 3,234,963 | 2/1966 | Lyon | 137/884 |
| 3,391,703 | 7/1968 | Kay | 137/884 |
| 3,602,246 | 8/1971 | Hettinger | 137/884 |
| 3,918,161 | 11/1975 | Morgan et al. | 32/22 |
| 4,456,168 | 6/1984 | Laakaniemi et al. | 137/884 X |
| 4,716,923 | 1/1988 | West | 137/312 |
| 4,980,130 | 12/1990 | Metzger et al. | 73/863.72 |
| 5,222,524 | 6/1993 | Sekler et al. | 137/884 |
| 5,234,032 | 8/1993 | Kline et al. | 137/884 |
| 5,273,074 | 12/1993 | Conradt et al. | 137/269 X |
| 5,341,846 | 8/1994 | Framberg | 137/884 |
| 5,462,087 | 10/1995 | Fukano et al. | 137/884 |

*Primary Examiner*—Hezron E. Williams
*Assistant Examiner*—Jay L. Politzer
*Attorney, Agent, or Firm*—Mark Z. Dudley

[57]     ABSTRACT

An analytical instrument preferably in the form of a chromatograph includes a computer, a pneumatic controller responsive to the computer, and planar manifold assembly. The planar manifold assembly includes one or more fluid-handling functional devices that may be surface mounted to a planar manifold. The fluid-handling functional device may be constructed as a valve, operable in response to a control signal from pneumatic controller for controlling fluid flow in selected fluid flow paths in the chromatograph, or as a sensor, a fluid regulator, a fluid flow input or output line, or the like.

6 Claims, 10 Drawing Sheets

PLANAR MANIFOLD ASSEMBLY

CROSS REFERENCE TO RELATED APPLICATION(S)

This is a continuation of application Ser. No. 08/376,614 filed on Jan. 23, 1995, now U.S. Pat. No. 5,567,868.

FIELD OF THE INVENTION

The present invention relates to methods and apparatus for the provision and control of fluid flow in an analytical apparatus, and more particularly with a planar manifold assembly in a gas chromatograph.

BACKGROUND OF THE INVENTION

Analytical instruments which rely upon regulated fluid flow are commonly employed in a wide variety of applications, such as sample purification, chemical analysis, clinical assay, and industrial processing. Such instruments typically function through devices which operate by initiating, maintaining, halting, or reversing a flow stream through the device. This may be accomplished by combinations of valves and/or pumps. Very often, such instruments devices require multiple flow paths to operate efficiently. Generally, efficient operation requires a flow system combining flow-through components, such as sorbent columns and connective tubing, with terminal components, such as needles, pumps, and drains. Different flow paths are frequently required to, for example, isolate a component from the flow system, include a component into the flow system, or rearrange the order of the components in the flow system. For many systems, an extensive and complex array of tubing, fittings, and the like are employed to provide the many flow paths that are necessary for optimum operation.

Combinations of commercially-available valves are often necessary to provide a number of flow paths among the flow-through components and terminal components employed in a flow system. Further, there is the need to sense certain characteristics of the fluid flow at differing points in the flow paths. Examples of such sensed characteristics include the pressure, flow rate, and temperature of the fluid. Other characteristics related to the particular fluid flow include the presence or absence of a fluid component, such as an analyte or contaminant. Such needs are typically addressed by the attachment of differing, plural sensors. There exists the practical problem, therefore, of connecting the large number of valves, sensors, fittings, and the like that are required for the multitude of flow path combinations in a modern analytical instrument.

Further, such flow systems involve a large number of flow-through and terminal fluid connections which increases the complexity, expense, and physical volume of the flow system. Such fluid connections are difficult to implement, especially when minimum volumes within the flow system are desirable. The complexity of such systems also introduces reliability concerns. Because the devices that are implemented in these flow systems are sometimes automated, the reliability and accessibility of the flow system are features critical to successful instrument operation.

Another problem involves the function of properly orienting all of the valves, sensors, and the like so as to allow the desired combinations of flow paths, yet also provide a flow system that is compact, easily-manufactured, inexpensive, and reliable. For example, the provision of fluid-tight connections in a complex fluid-handling assembly has become exceedingly problematic as the assembly is reduced in size. Some instruments, such as a gas chromatograph, employ fluids in the form of combustible gasses in performing an analysis. Even though the pneumatic fittings in the typical chromatograph are designed to minimize leakage, one may nonetheless consider a pneumatic fault mode wherein a gas leak could occur and sufficient gas could accumulate so as to pose an unsafe condition.

It will also be appreciated that a flow system must be versatile, that is, capable of being reconfigured during an instance of repair or modification, or to meet the requirements of a particular application as additional valves, fittings, etc. are added to the flow system.

SUMMARY OF THE INVENTION

The advantages of the invention are achieved in a first preferred embodiment of an analytical instrument, preferably in the form of a chromatograph, that includes a computer, a pneumatic controller responsive to the computer, and planar manifold assembly. The planar manifold assembly includes one or more fluid-handling functional devices attached to a planar manifold. The fluid-handling functional device may be surface mounted to the planar manifold and may be constructed as a valve, operable in response to a control signal from pneumatic controller for controlling fluid flow in selected fluid flow paths in the chromatograph, or as a sensor, a fluid regulator, a fluid flow input or output line, or the like.

BRIEF DESCRIPTION OF THE DRAWINGS

The present invention will be better understood, and its numerous objects and advantages will become apparent by reference to the following detailed description of the invention when taken in conjunction with the following drawings, in which.

DETAILED DESCRIPTION OF THE PREFERRED EMBODIMENT

The present invention will find useful application in a variety of analytical systems that benefit from fluid control of one or more fluid streams. The apparatus and methods of the present invention may be employed in particular to provide initiation, distribution, redirection, termination, control, sensing, and other types of functions (collectively defined herein as fluid-handling functions) with respect to one or more fluid streams. Gases are the preferred fluids according to the practice of the present invention, and therefore the following description of the invention will include a description of the arrangement, construction, and operation of certain pneumatic devices, and hence is particularly directed to the control of a plurality of gaseous streams in an inlet or detector in a gas chromatographic analytical system (hereinafter, a chromatograph). However, for the purposes of the following description, the term "pneumatic" will also be considered to refer to all types of fluids.

Further examples that are particularly benefited by use of the present invention include supercritical fluid chromatography and high-pressure gas chromatography (HPGC). However, it should be understood that the teachings herein are applicable to other analytical instruments, including liquid chromatographs, high-pressure liquid chromatographs (HPLC), clinical analyzers, flow-injection analyzers, laboratory water purification systems, syringe-type reagent dispensers, manual and automated solid phase extraction (SPE) instruments, supercritical fluid extraction (SFE) instruments, stopped-flow spectrophotometers, automated protein or nucleic acid sequencers, and solid phase protein or nucleic acid synthesizers.

Figure 1:
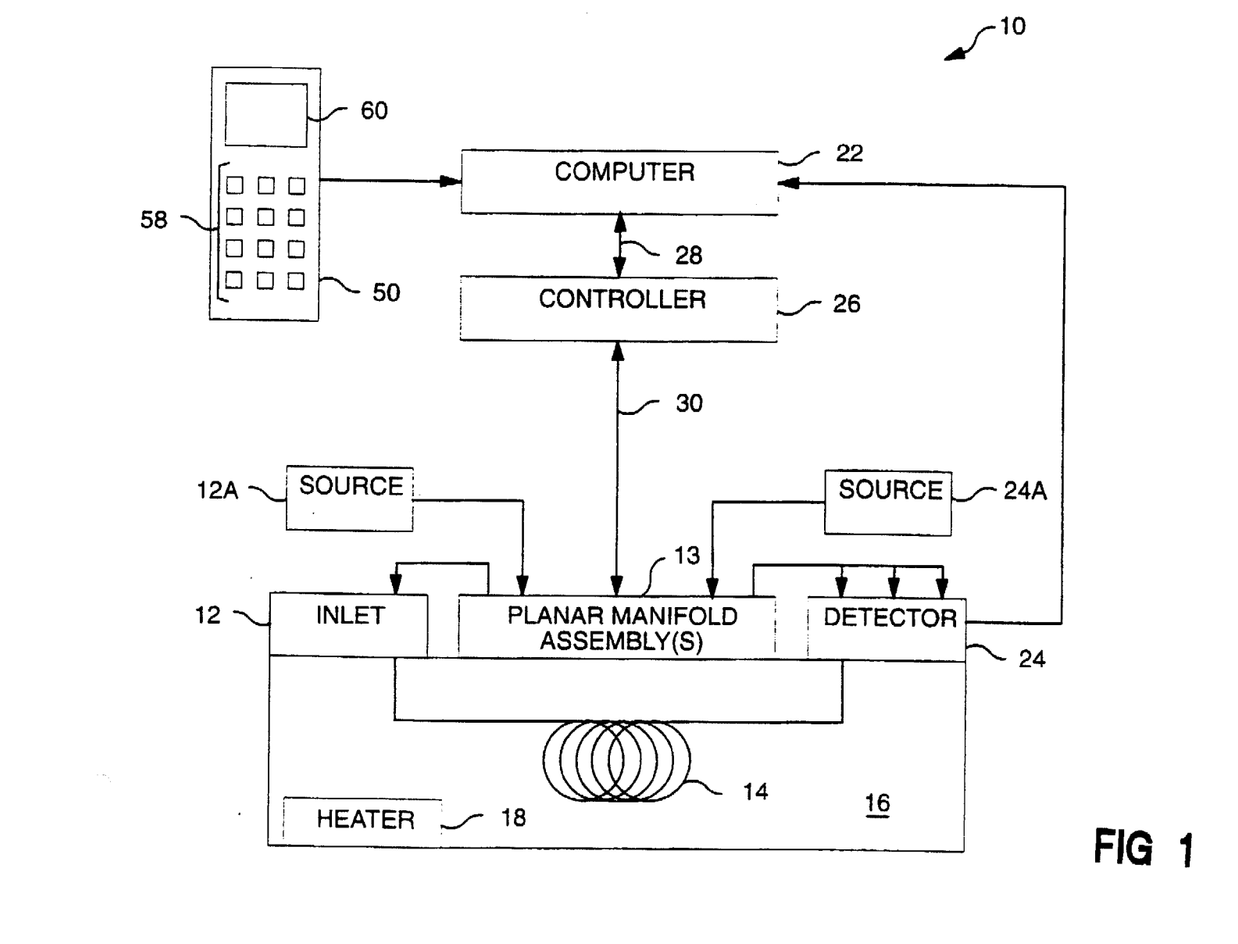
FIG. 1 is a simplified block diagram of an analytical instrument constructed in accordance with the present invention.

A new and novel analytical instrument is shown in FIG. 1 and is generally designated chromatograph 10. In order to perform a chromatographic separation of a given sample compound, a sample is injected with a pressurized carrier gas by means of an inlet 12. The carrier gas supplied to inlet 12 is provided from a source 12A through one or more planar manifold assembly(s) 13, each of which serves in part to control and redirect a plurality of gas flows, including the carrier gas and a plurality of detector gasses of appropriate types, such as air, hydrogen, and make-up gas. The detector gases are provided from respective sources (one such source 24A is shown) to the planar manifold assembly 13. Suitable fluid-handling functional devices, such as fittings, regulators, valves, sensors, and the like in the planar manifold assembly 13 may be passive (such as a termination fitting) or active and hence operated under the control of the computer 22 by way of control signals provided on a data and control lines 28, 30. For example, the pneumatic controller 26 effects control of, among other things, fluid flow rate, fluid pressure, fluid flow regulation, and the continuity or discontinuity of flow. As further example, the time during which a particular valve in the planar manifold assembly 13 will remain open and closed in relation to control signals received on the data and control line 28 and in accordance with certain operating conditions of the chromatograph 10. The control and data line 30 also allows the return of sense information from appropriate signal-interface electronics that connect to the valves, sensors, etc. that are provided in the planar manifold assembly 13. Accordingly, the computer 22, pneumatic controller 26, and planar manifold 13 may be operated to effect a variety of fluid handling functions that heretofore have been difficult to achieve in conventional fluid-handling apparatus.

A column 14 is positioned within an oven 16. The carrier gas/sample combination passing through column 14 is exposed to a temperature profile resulting in part from the operation of a heater 18 within oven 16. During this profile of changing temperatures, the sample will separate into its components primarily due to differences in the interaction of each component with the column 14 at a given temperature. As the separated components exit the column 14, they are detected by a detector 24.

Computer 22 maintains overall control of all systems associated with gas chromatograph 10. It will be recognized that any particular gas chromatograph may include more systems than those described in relation to the present invention. It will also be understood that although computer 22 is shown as a single block, such computer includes a central processing unit and all associated peripheral devices, such as random access memories, read-only memories, input/output isolation devices, clocks and other related electronic components. In the preferred embodiment, the central processor used in computer 22 is a microprocessor. As such, computer 22 includes a memory in which information and programming can be stored and retrieved by known methods. However, it will be appreciated that the programmed control of pneumatic controller 26 can be implemented by other computing means, such as an embedded microprocessor or dedicated controller circuit incorporated in the pneumatic controller 26. Also, the programming associated with computer 22 that is utilized in relation to the present invention will be readily understood from the description herein.

An electronic control panel 50 is shown to include at least two main input/output components, namely a keypad 58, and a display 60. By monitoring the operation of the chromatograph 10 by signals from certain components, such as the detector 24, the computer 22 can initiate and maintain certain functions required for an analytical run. Consequently, indicating or prompt messages can be generated by computer 22 and displayed on display 60. Operating commands and other information are entered into computer 22 by way of keypad 58.

Figure 2:
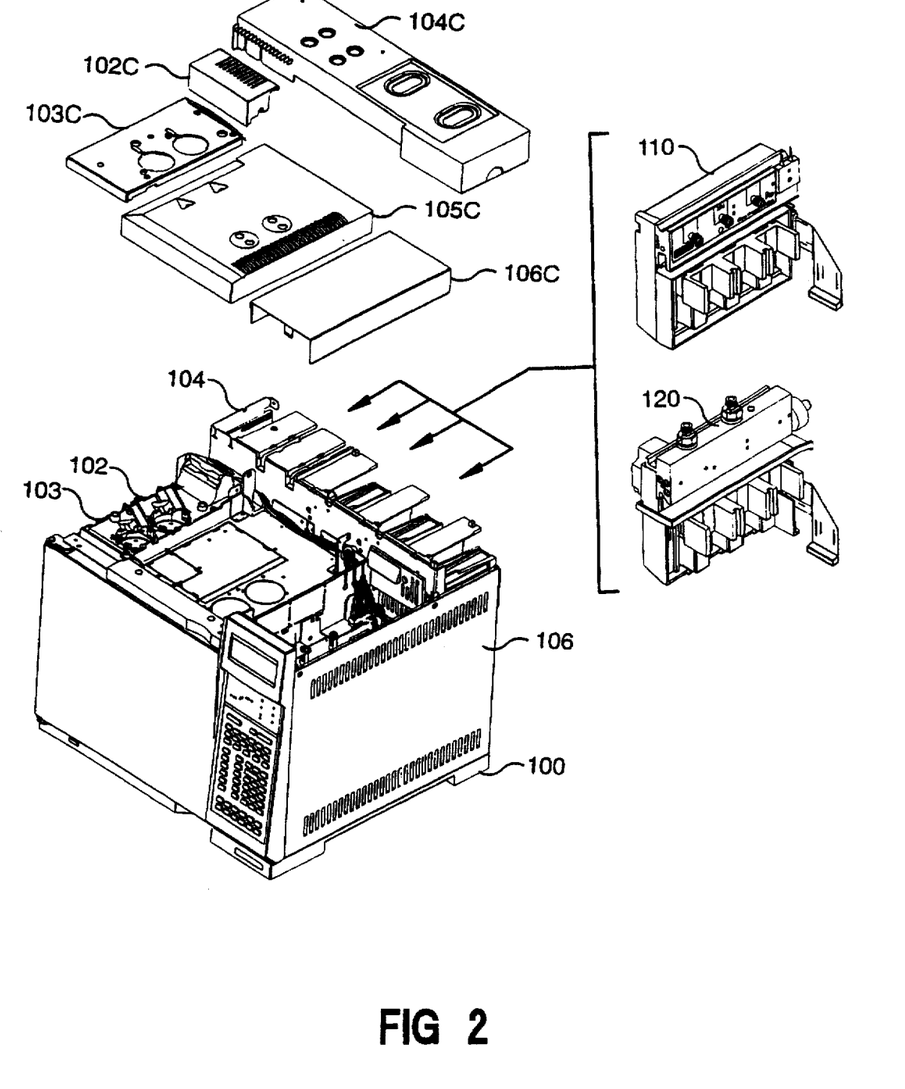
FIG. 2 is a side perspective view of preferred embodiment of the analytical instrument of FIG. 1, constructed as a chromatograph.

FIG. 2 illustrates a preferred embodiment 100 of the chromatograph 10 of FIG. 1. In the preferred embodiment, the chromatograph 100 is a Hewlett-Packard HP6890 gas chromatograph. The chromatograph 100 includes an inlet port fan 102 and respective cover 102C, an inlet port section 103 and respective cover 103C, a pneumatics section 104 and respective cover 104C, a detector section 105 and respective cover 105C, and an electronics section 106A and respective cover 106C. According to a feature of the present invention, the pneumatics section 104 includes provision for the installation and operation of a plurality of the planar manifold assembly 13 of FIG. 1. In particular, the plurality may include a first planar manifold assembly 110 specifically designed for use in fluid-handling functions that relate to one or more detectors 24, and second planar manifold assembly 120 designed for use in fluid-handling functions that relate to one or more inlets 12. Thus, and in accordance with another feature of the present invention, the planar manifold assembly 13 may be configured to perform fluid-handling functions for a specific portion of the chromatograph 100.

Figure 3A:
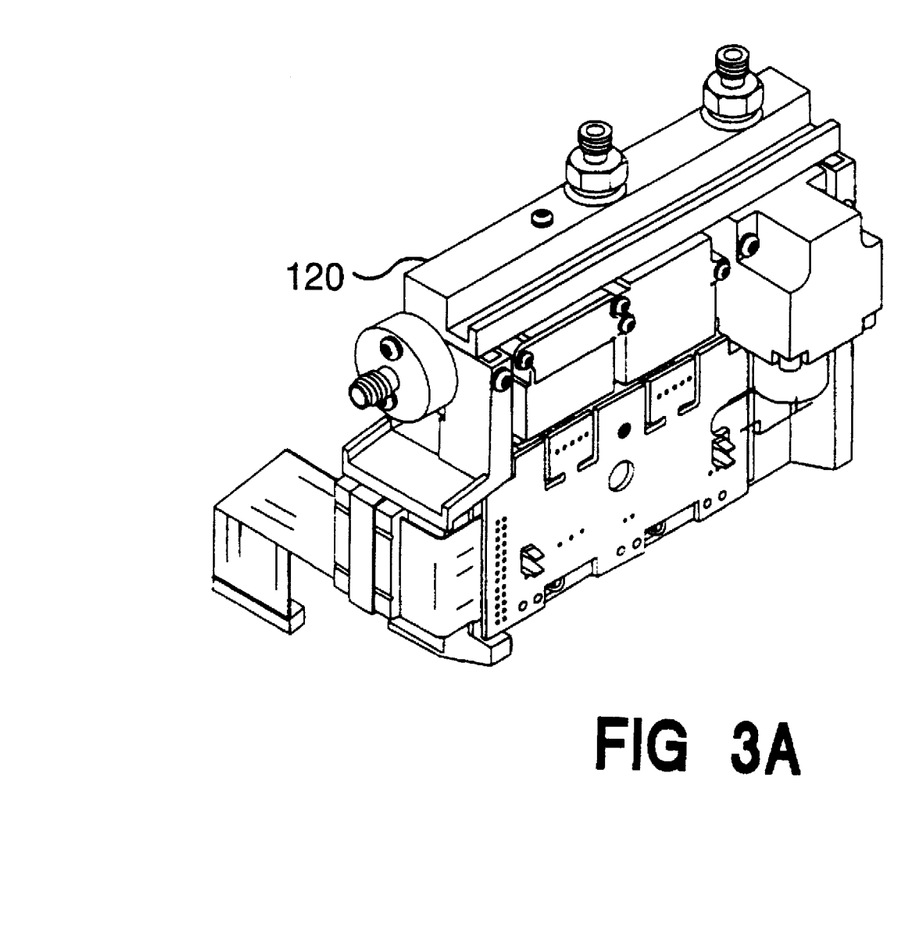
FIGS. 3A and 3B are front and rear perspective views, respectively, of a preferred embodiment of a planar manifold assembly operable in the chromatograph of FIG. 2.
Figure 3B:
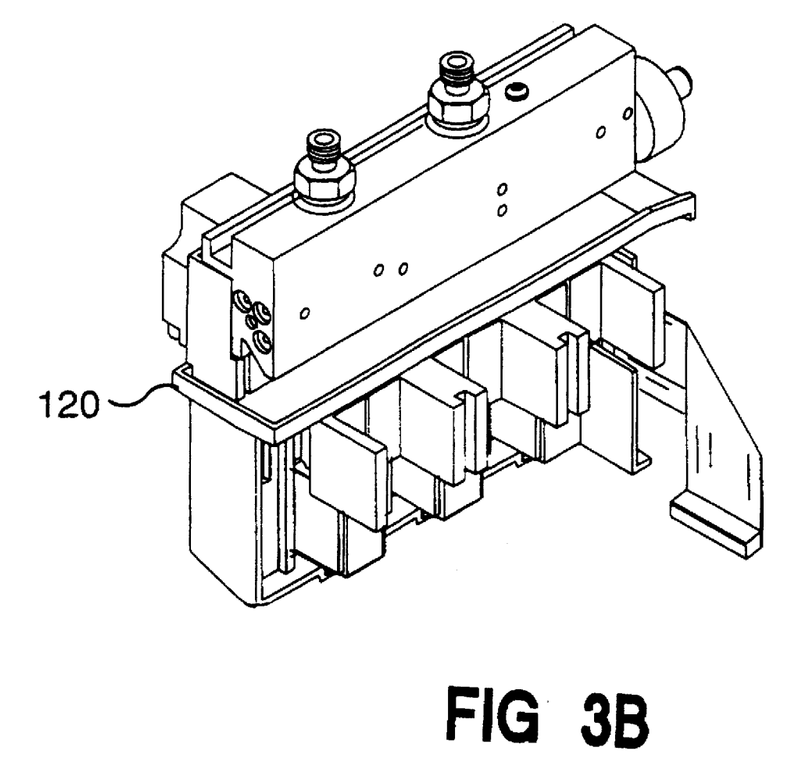
Figure 4A:
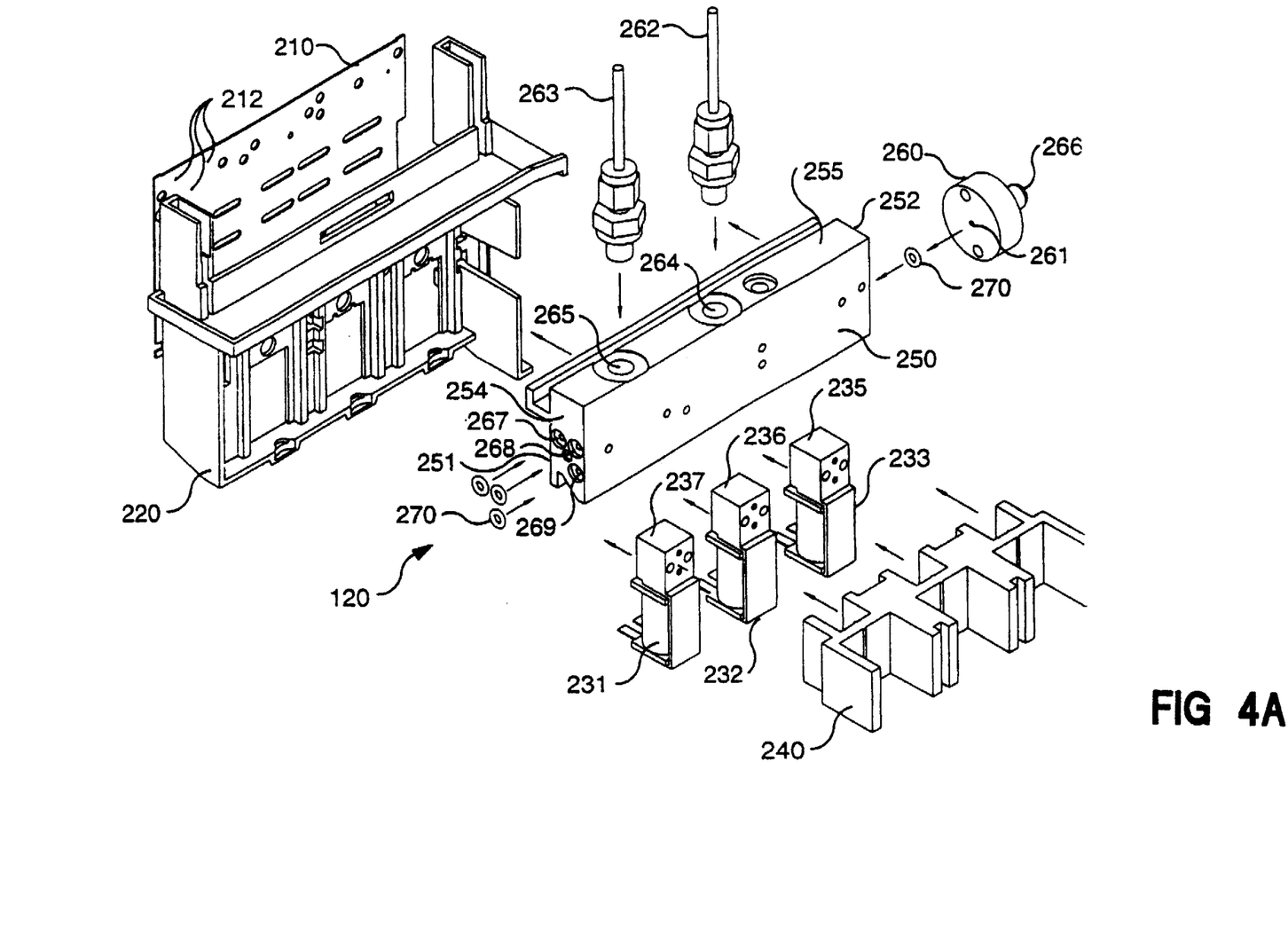
FIG. 4A is side perspective view of a first exploded portion of a planar manifold assembly preferred for use in the chromatograph of FIG. 2.
Figure 4B:
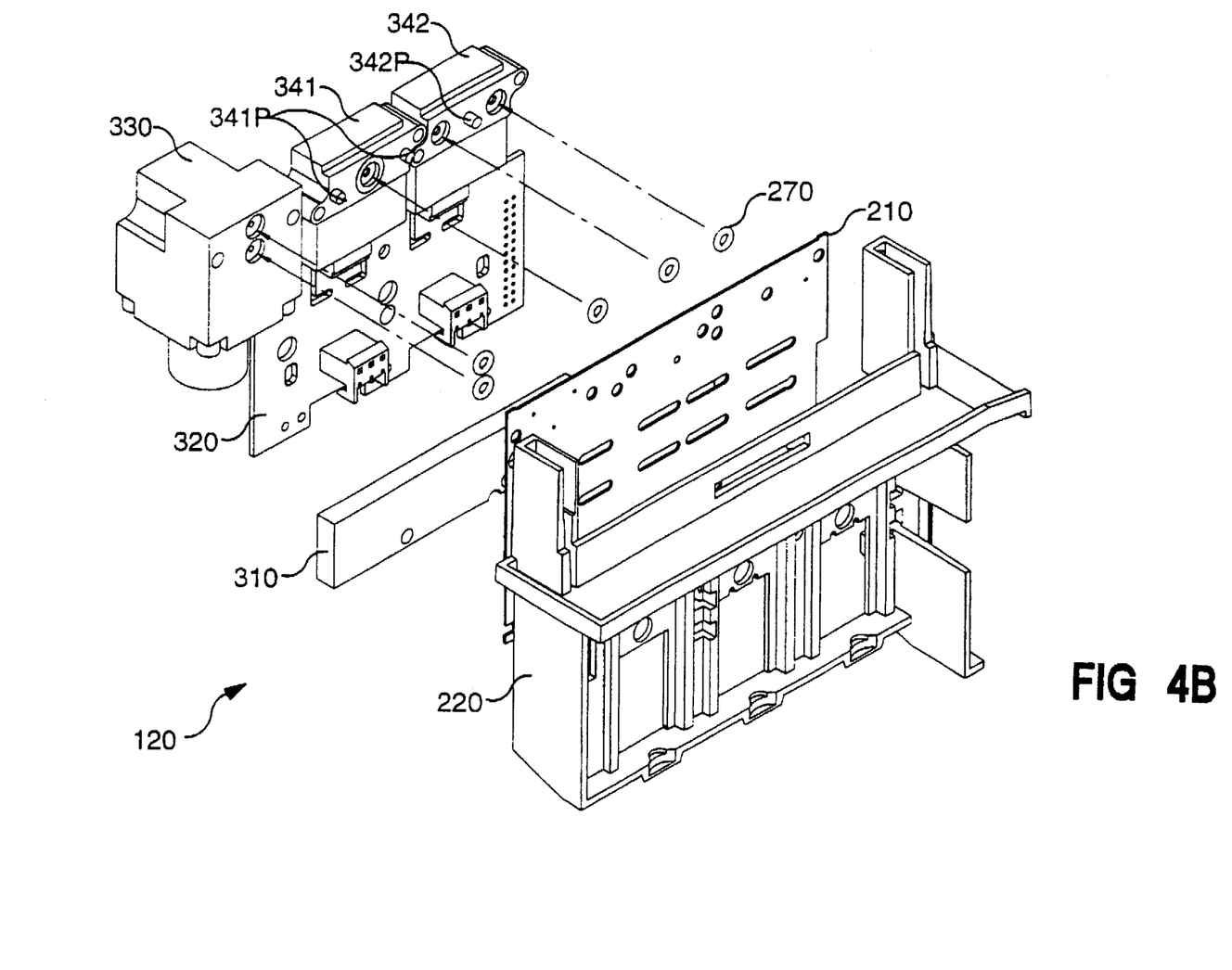
FIG. 4B is side perspective view of a second exploded portion of the same planar manifold assembly, with certain components of the planar manifold assembly being common to both FIGS. 4A and 4B for clarity.
Figure 5A:
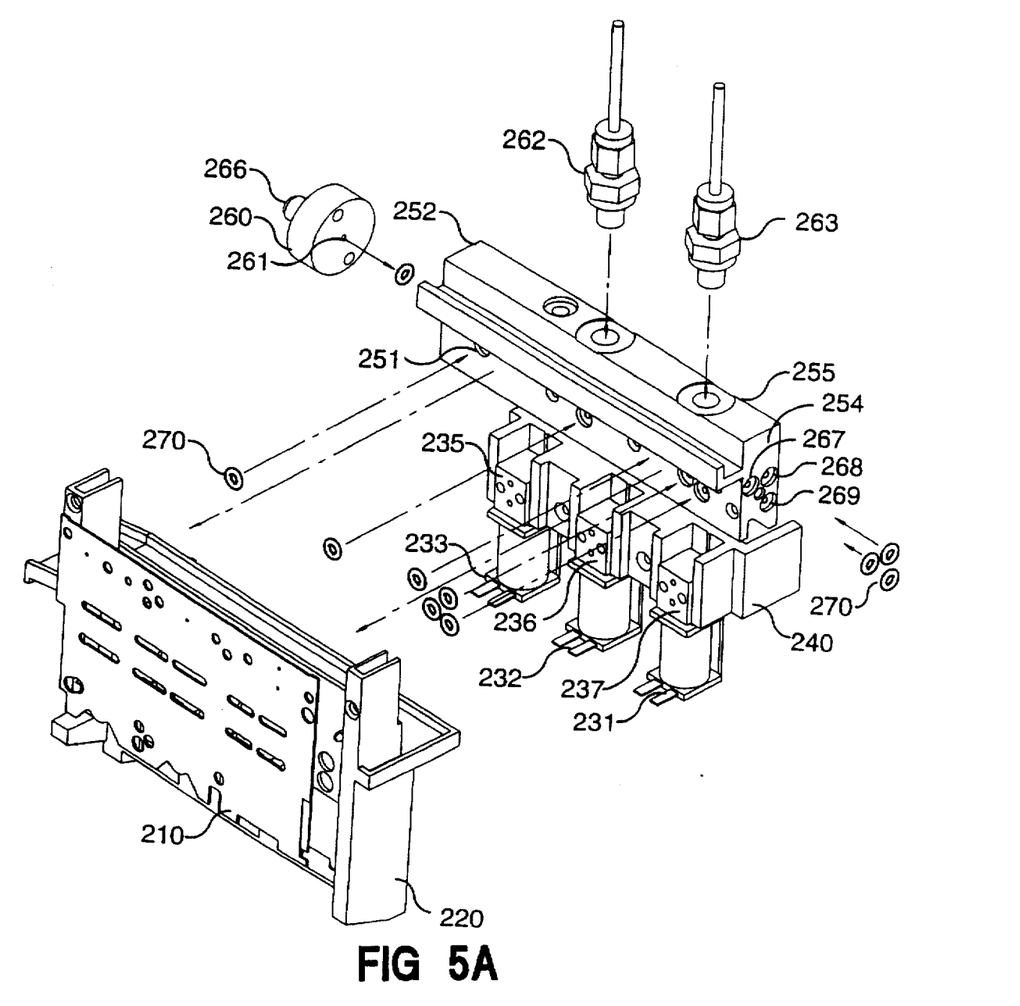
FIG. 5A is another side perspective view of the first exploded portion of the planar manifold assembly of FIG. 2.
Figure 5B:
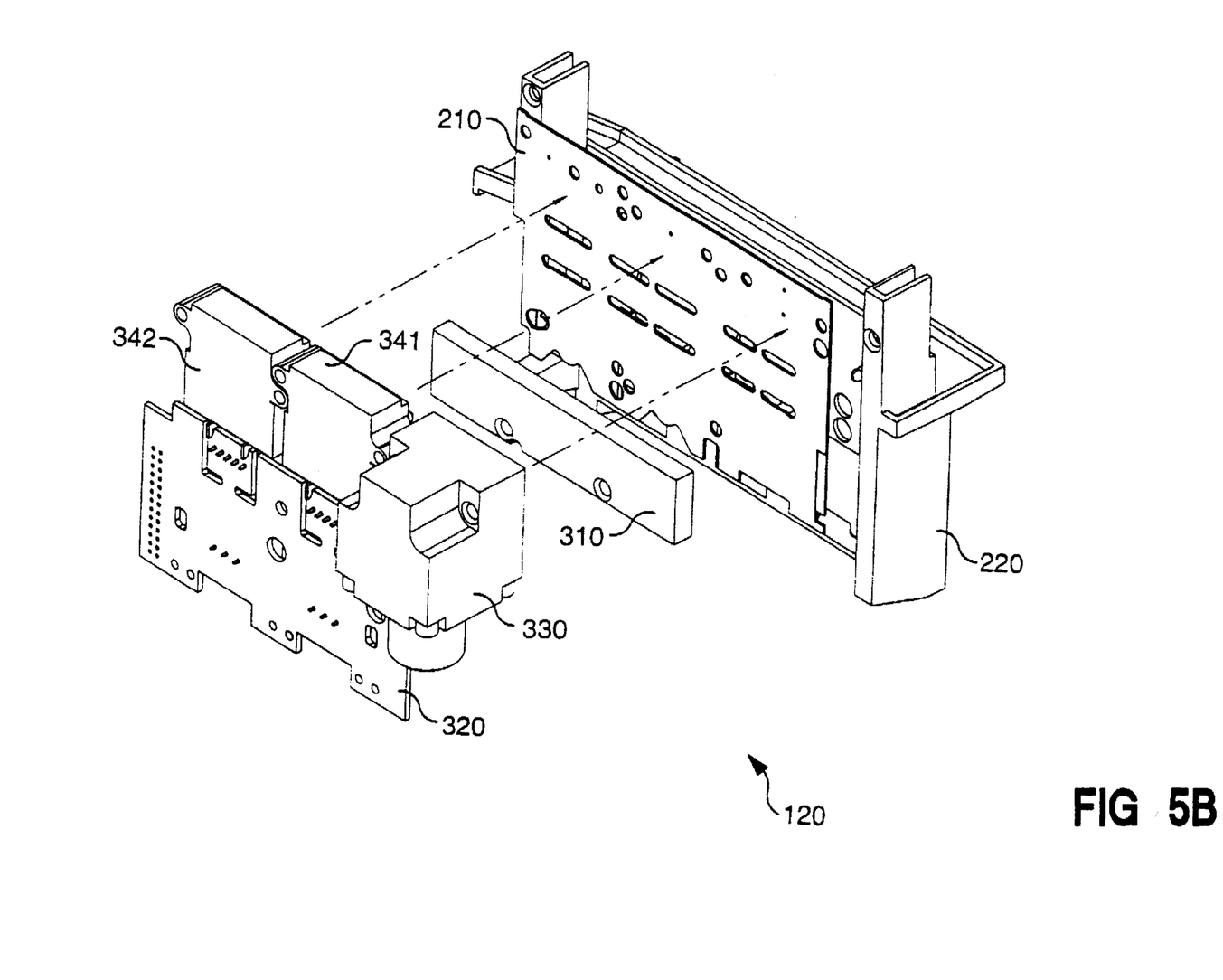
FIG. 5B is another side perspective view of the second exploded portion of the same planar manifold assembly, with certain components of the planar manifold assembly being common to both FIGS. 5A and 5B for clarity.

FIGS. 3–5 illustrate in greater detail the second planar manifold assembly 120 of FIG. 2. The illustrated embodiment is accordingly constructed for use with the inlet 12 of the chromatograph 10 of FIG. 2. With reference again to FIG. 1, however, it should be understood that the description and techings herein may be applied as well to the construction of a planar manifold assembly for use with fluid-handling functions associated with the operation of the detector 24, the column 14, or another portion of the chromatograph 10.

The second planar manifold assembly 120 includes a planar manifold 210, an inlet manifold chassis 220, a first valve 231, a second valve 232, a third valve 233, a valve clamp 240, a fitting block 250, and a supply fitting 260. The fitting block includes a longitudinal port surface 251, a first lateral port surface 252, a second lateral port surface 254, and an upper port surface 255. A split vent line 262 and a septum purge vent line 263 are attachable to respective vents 264, 265 in the upper port surface 255 in fitting block 250. The second planar manifold assembly 120 includes a valve backing plate 310, a data and control signal interface board 320, a flow controller 330, a first sensor 341, and a second sensor 342.

In the preferred embodiment, the first valve 231 is constructed as a solenoid valve; the second valve 232 and the third valve 233 are each constructed as proportional valves; the flow controller 330 is constructed as a purge flow controller; and the first sensor 341 is constructed as a pressure sensor and the second sensor 342 is constructed as a flow sensor. Further, the supply fitting 260 is constructed to receive carrier gas from a supply line (not shown) at a supply line fitting 266. The supply fitting 260 attaches to the first lateral port surface 252 in the fitting block 250 so as to transfer a flow of carrier gas from a through hole 261 into a port (not shown) on the first lateral port surface 252 in the fitting block 250. The supply fitting also includes an internal frit (not shown). That is, the fitting block 250 is constructed to include a plurality of internal, fluid-bearing passageways that are accessible at respective ports on several of the surfaces of the fitting block 250.

Each port on the fitting block 250 is recessed to allow use of an O-ring 270 for face-sealing the planar manifold 210, or a particular fluid-handling functional device, to the fitting block 250. For example, a septum purge line port 267, a carrier gas port 268, and a split vent line port 269 are located in the second lateral port surface 254 and receive respective O-rings 270; a plurality of ports in the first longitudinal port surface 251 receive respective O-rings 270 when mated to respective ports 212 on the planar manifold 210.

The inlet manifold chassis 220 aids in aligning the fitting block 250 and the valves 231, 232, 233 to the planar manifold 210. The first valve 231, second valve 232, and third valve 233 are clamped to the planar manifold 210 by the valve clamp 240 with the aid of suitable means known in the art, such as fasteners (not shown), that pass through the valve backing plate 310 and appropriate through-holes in the planar manifold 210, so as to be secured by suitable means, such as threaded apertures, in the valve clamp 240. The respective valve block faces 235, 236, 237 are thus face-sealed to the planar manifold 210. The longitudinal port surface 251 of the fitting block 250 is similarly clamped to the planar manifold 210 by way of suitable fasteners (not shown).

Figure 6:
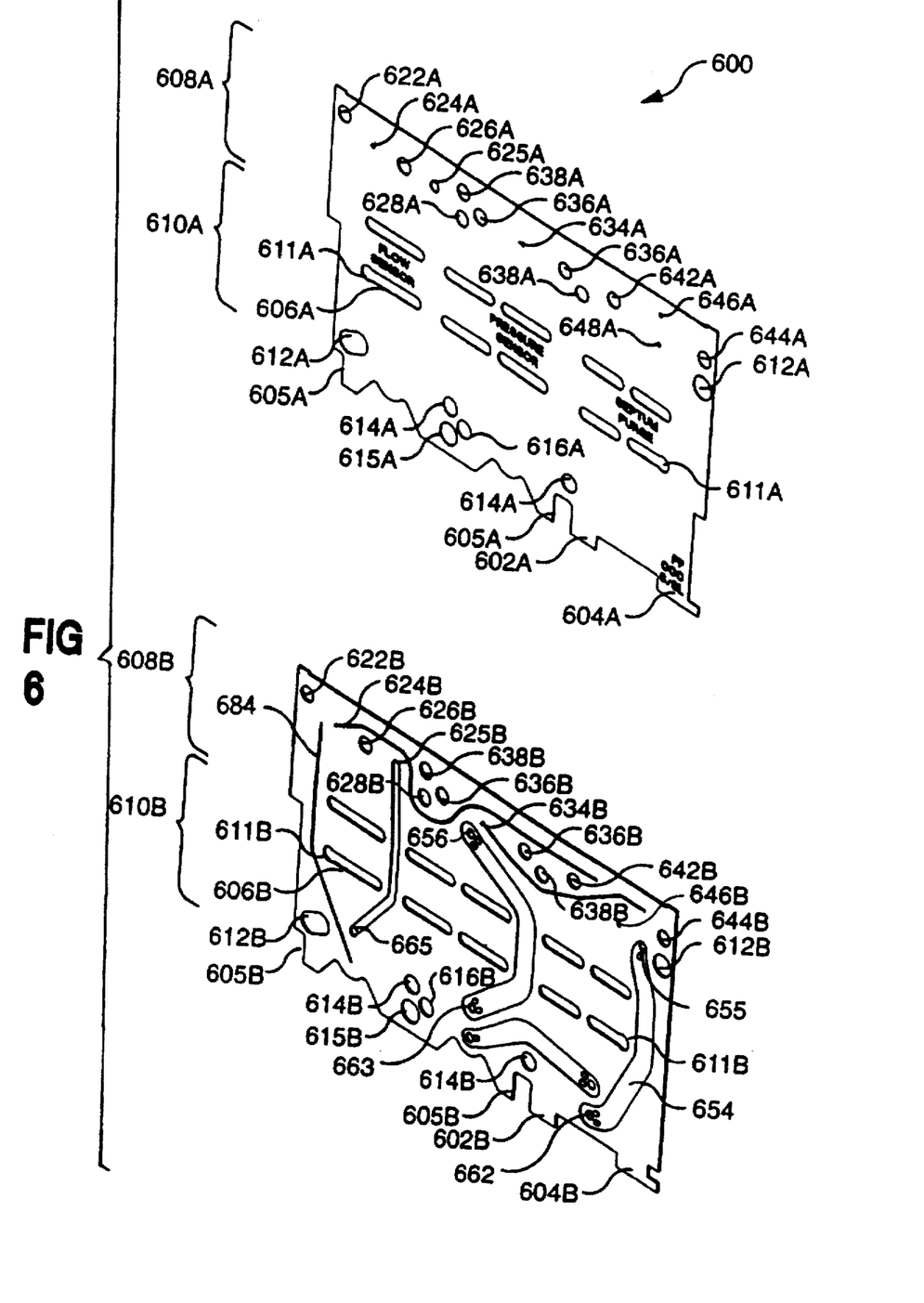
FIG. 6 is a side perspective view of the planar manifold operable in the planar manifold assembly of FIGS. 3–5, illustrating front and back portions of the planar manifold in exploded view for clarity.
Figure 7:
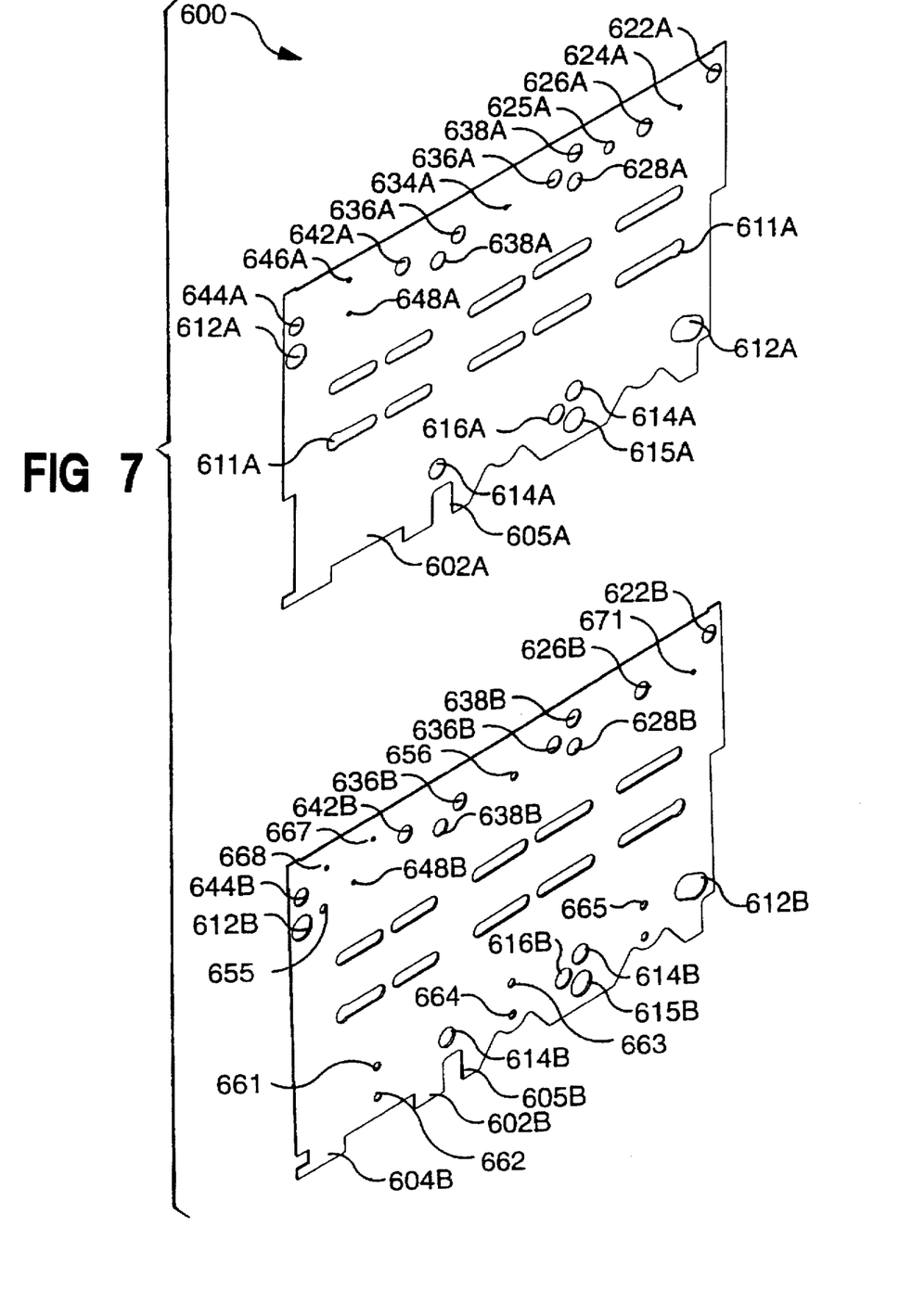
FIG. 7 is another side perspective view of the planar manifold of FIG. 6, also illustrating the front and back portions of the planar manifold in exploded view for clarity.

FIGS. 6 and 7 illustrate a preferred embodiment of a planar manifold 600 contemplated by the present invention. A front plate 602A and a back plate 602B may be seen to be sized and constructed to be superimposed and bonded together during the manufacturing process to form the planar manifold 600. Preferably, the front plate 602A and back plate 602B are machined from stainless steel and etched to provide an arrangement of features, discussed below, before being bonded together. The preferred method of bonding is diffusion bonding, which generally is known in the art and is described in, for example, U.S. Pat. No. 3,530,568, the disclosure of which is included herein by reference. However, in other embodiments, other materials and bonding methods may be employed, and a number of etched intermediary plates (such as one, two, or more, not shown) are also contemplated being provided intermediate the front plate 602A and back plate 602B to form a multi-layer configuration.

A notch 604B in the rear plate 602B is included at manufacture to correspond with one of several indicia 604A inscribed on the front plate 602A so as to define a particular pneumatic configuration that is served by the planar manifold 600. In the illustrated embodiment, the notch 604B indicates by its location that the planar manifold 600 is intended for use in a split/splitless (S/SL) inlet configuration, and accordingly the description herein is directed to the planar manifold assembly 120 constructed for use in a chromatograph 10 having such an inlet configuration. Upon modifications to the back plate 602B, there are contemplated other preferred embodiments of the planar manifold assembly 120 that are designed for use in cool on-column (COC) or purged pack (PP) inlet configurations. It is a feature of the present invention that the construction of the front plate 602A is common to all of the named inlet configurations, and that the back plate 602B will vary in its construction according to the type of inlet configuration that is to be served. This feature thus makes the front plate 602A a more versatile piece part, thus lowering the parts count and reducing manufacturing costs. In addition, the location of the notch 604B can be sensed during assembly of the planar manifold assembly to ensure that the planar manifold 210 has been properly configured for the particular inlet configuration.

Each of the front plate 602A and the rear plate 602B include a variety of other physical features for accommodating certain mechanical functions. Notches 605A and 605B serve to accommodate a locating protrusion (not shown) on the inlet manifold chassis 220 for mounting the data and control signal interface board 320. Oblong openings 606A, 606B are distributed longitudinally to effect a thermal break between the plate upper portions 608A, 608B and the plate lower portions 610A, 610B. Locator holes 611A, 611B are provided for locating the planar manifold 600 on respective protrusions (not shown) on the inlet manifold chassis 220; tooling holes 612A, 612B are used during construction of the planar manifold 600. Through-holes 614A, 614B allow passage therethrough of the fasteners used to clamp the valve clamp 240 to the valve backing plate 310, and through-holes 615A, 615B allow a protrusion on the inlet manifold chassis 220 to support the data and control signal interface board 320. Clearance holes 616A, 616B, are provided for accommodating respective protrusions (not shown) on the inlet manifold chassis 220 so as to properly orient the valve backing plate 310.

Plate upper portions 608A, 608B include several features common to both pieces so as to receive certain fluid-handling functional devices already described. In particular, to accommodate attachment of the flow sensor 342, there are provided: fastener through-holes 622A, 622B; a pneumatic output 624A and a corresponding first minor pneumatic channel 624B; pneumatic input 625A and corresponding first major pneumatic channel 625B; locating holes 626A, 626B to accommodate a protrusion 342P; and fastener through-holes 628A, 628B. To accommodate attachment of the pressure sensor 341, there are provided: a pneumatic output 634A and a corresponding third minor pneumatic channel 634B; locating holes 636A, 636B that accommodate plural protrusions 341 P; and fastener through-holes 638A, 638B. To accommodate attachment of the purge flow controller 330, there are provided: fastener holes 642A, 642B, 644A, 644B; a pneumatic input 46A which communicates with the third minor pneumatic channel 634B; and pneumatic outputs 648A, 648B which communicate with a channel in the fitting block 250.

In addition to the first major pneumatic channel 625B, there is a second major pneumatic channel 652, a third major pneumatic channel 653, and a fourth major pneumatic channel 654. The fourth major pneumatic channel 654 communicates with the fitting block 250 at an upper output 655 and also communicates with the first valve 231 at a lower output 662. The second major pneumatic channel 657 communicates with the fitting block 250 at an upper output 656 and also communicates with the second valve 232 at a lower output 663. The first major pneumatic channel communicates with the pneumatic input 625A and the third valve 233 at a lower output 665. The third major pneumatic channel 653 communicates with the first valve 231 at an upper output 661, and also communicates with the second valve 232 at a lower output 664. A second minor pneumatic channel 684 communicates with a carrier gas input 671 and the third valve 233 at a lower output 666. The first minor pneumatic channel 624B also communicates with the fitting block 250 at an upper output 667. The third minor pneumatic channel 634B communicates with the fitting block 250 at an upper output 668.

The advantages of the planar manifold assembly of the present invention include the reduction of external connections between fluid-handling functional devices (such as fittings, valves, sensors, and the like) by use of a single planar manifold for the provision of a plurality of flow paths. The fluid-handling functional devices that connect to the planar manifold are preferably constructed to be surface-mounted, which has been found to offer reliable, fluid-tight connection without the complexity and difficulty of conventional pneumatic connections. The number and complexity of external connections, which would otherwise undesirably increase the volume of the flow system, are also decreased. Another advantage is that the reliability of the pneumatic connections is improved.

A further advantage of the present invention is that multiple fluid-handling functional devices may be coordinated and assembled in a smaller volume than is possible in prior art systems. This results from the pneumatic channels that are integrated in the planar manifold, and thus many of the fluid flow paths are integral to the planar manifold, which is itself quite compact and amenable to construction in a variety of shapes and configurations. For example, it is contemplated that the planar manifold may be constructed in an irregular shape, such as a curved, bent, or multiply-angled configuration, so as to conform to an irregularly-shaped, compact volume.

A large number of fluid-handling functional paths may be integrated into the planar manifold that heretofore would be difficult if not impossible to assemble using traditional tubular pipe, ferrules, and manual firings. Also, considerable cost savings and improved reliability are realized by reduction of the number of connections necessary to achieve multiple flow paths.

The surface-mounted pneumatic connections provided by the invention also reduce the complexity of a flow system, which is desirable during the stages of manufacturing, assembly, repair, or modification of the analytical instrument in which the planar manifold assembly may be situated.

While the invention has been described and illustrated with reference to specific embodiments, those skilled in the art will recognize that modification and variations may be made without departing from the principles of the invention as described herein above and set forth in the following claims.

What is claimed is:

1. An analytical instrument for detecting the presence of an analyte in a sample fluid, comprising:
   an inlet for injecting the sample fluid into a carrier fluid to provide a fluid mixture;
   a separation column for receiving the fluid mixture and for performing a chromatographic separation of the analyte;
   a detector for detecting the elution of the analyte from the separation column; and
   a planar manifold assembly for providing a plurality of fluid-handling functions with respect to at least one of the sample fluid, carrier fluid, and fluid mixture, comprising:
     a planar manifold including first and second plates, each of said plates having inner and outer surfaces, said first and second plates being joined at their respective inner surfaces such that their outer surfaces form respective first and second manifold outer surfaces, a plurality of pneumatic channels located in the inner surface of the first plate, and said channels communicating with a selected one of the first and second manifold outer surfaces at respective manifold ports;
     a plurality of fluid-handling functional devices each of which having a face and at least one device port on the face; and
     means for attaching the face to the selected one of the first and second manifold outer surfaces so as to effect a fluid-tight connection between said device port and one of said manifold ports;
   wherein said plurality of fluid-handling functions is performed according to a configuration of the fluid-handling devices, the pneumatic channels, and the manifold ports.

2. The analytical instrument of claim 1, wherein the configuration is predetermined according to the path of a fluid flow in a selected one in a group consisting of the inlet, detector, and separation column.

3. The analytical instrument of claim 1, wherein the plurality of fluid-handling functional devices includes a first fluid-handling functional device for performing a first fluid-handling function and a second fluid-handling functional device for performing a second, differing fluid-handling function, and wherein each of said first fluid-handling functional device and said second fluid-handling functional device is selected from a group including: valves, sensors, flow controllers, and fluid fittings.

4. The analytical instrument of claim 1, wherein each of the inner surfaces of the first and second plates further comprise a material susceptible to bonding by a diffusion bonding process, and wherein the inner surfaces are bonded together according to the diffusion bonding process.

5. The analytical instrument of claim 1, wherein the operation of one of said fluid-handling functional devices is associated with an electronic signal, and further comprising a pneumatic controller for providing the electronic signal.

6. The analytical instrument of claim 1, wherein the operation of one of said fluid-handling functional devices is associated with an electronic signal, and further comprising a computer for providing the electronic signal.

* * * * *